(12) United States Patent
Gong

(10) Patent No.: US 9,603,905 B2
(45) Date of Patent: Mar. 28, 2017

(54) INTRANASAL INSULIN ADMINISTRATION FOR THE MINIMIZATION OF ANESTHESIA-INDUCED MEMORY LOSS

(71) Applicant: The Research Foundation for Mental Hygiene, Inc., Menands, NY (US)

(72) Inventor: Cheng-Xin Gong, Staten Island, NY (US)

(73) Assignee: THE RESEARCH FOUNDATION FOR MENTAL HYGIENE, INC, Menands, NY (US)

( * ) Notice: Subject to any disclaimer, the term of this patent is extended or adjusted under 35 U.S.C. 154(b) by 0 days.

(21) Appl. No.: 14/656,975

(22) Filed: Mar. 13, 2015

(65) Prior Publication Data

US 2015/0258178 A1 Sep. 17, 2015

Related U.S. Application Data

(60) Provisional application No. 61/952,257, filed on Mar. 13, 2014.

(51) Int. Cl.
*A61K 38/28* (2006.01)
*A61K 9/00* (2006.01)

(52) U.S. Cl.
CPC ............ *A61K 38/28* (2013.01); *A61K 9/0043* (2013.01)

(58) Field of Classification Search
CPC ...................................................... A61K 38/28
See application file for complete search history.

(56) References Cited

PUBLICATIONS

Cheney et al., Anesthesiology, 90: 1062-1069, 1999.*
Lee et al., Anesthesiology, 101: 145-152, 2004.*
Ott et al., Diabetes Obesity and Metab. 14:214-221, 2012.*
Zurek et al., Anesthesia and Analgesia, 114: 845-855, 2012.*
Kidambi et al., BMC Res. Notes, 3: 201, 2010.*
Sprung et al, ScienceDaily release, 2 pages, May 2013.*

* cited by examiner

*Primary Examiner* — Gyan Chandra
(74) *Attorney, Agent, or Firm* — David L. Nocilly; Bond, Schoeneck & King, PLLC

(57) ABSTRACT

Intranasal administration of insulin for a predetermined period prior to anesthesia significantly prevented anesthesia-induced tau hyperphosphorylation and cognitive impairment and enhanced brain insulin signaling in mice. Intranasal insulin thus provides a treatment for prevention of anesthesia-induced tau pathology and increased risk for tauopathies in surgical patients and may be administered to a subject prior to anesthesia, such as by administering several doses of intranasal insulin for several consecutive days prior to any anesthesia.

6 Claims, 18 Drawing Sheets

INTRANASAL INSULIN ADMINISTRATION FOR THE MINIMIZATION OF ANESTHESIA-INDUCED MEMORY LOSS

CROSS-REFERENCE TO RELATED APPLICATIONS

The present application claims priority to U.S. Provisional Application No. 61/952,257, filed on Mar. 13, 2014.

BACKGROUND OF THE INVENTION

1. Field of the Invention

The present invention relates to the prevention of anesthesia-induced tau pathology and cognitive impairment and, more particularly, to an intranasal administration of insulin that prevents abnormal hyperphosphorylation of tau and cognitive impairment.

2. Description of the Related Art

Tauopathies are a family of age-associated neurodegenerative diseases which are characterized histopathologically by the abnormal hyperphosphorylation and aggregation of tau in the brain, and clinically by cognitive impairment and/or motor dysfunction. Tauopathies include frontotemporal dementia with Parkinsonism linked to chromosome-17 (FTDP-17), corticobasal degeneration, Pick disease, progressive supranuclear palsy, Guam Parkinsonism dementia complex, dementia pugilistica also known as chronic traumatic encephalopathy or traumatic brain injury, ceroid neuronal lipofuscinosis, Hallerworden Sptaz disease, Alzheimer's disease and adults with Down syndrome. The abnormal hyperphosphorylation of tau results in not only the loss of microtubule assembly promoting and stabilizing protein function, but also a gain of toxic function; the abnormally hyperphosphorylated tau sequesters normal tau as well as the other two microtubule associated proteins (MAPs), MAP1 and MAP2, and causes disruption of microtubules.

The majority of tauopathy cases have the sporadic form of the disease. It is well established that elderly individuals are at increased risk of cognitive decline after anesthesia or surgery. Though the long-term effect of anesthesia on cognition is still under debate, anesthesia may accelerate pre-existing but asymptomatic neurodegenerative changes in the brain and thus promote the development of a tauopathy. Evidence from animal models suggests that anesthetic exposure can increase tau hyperphosphorylation, and cause significant learning and memory deficits in aged rodents.

Impaired brain insulin signaling pathways have been implicated in the development of Alzheimer's disease (AD), a common tauopathy. Decreases in the levels and activities of several components of the insulin signaling pathway have been found in AD brain. In agreement with the proposed role of insulin signaling in cognition, intranasal administration of insulin has been reported to improve memory in healthy humans and in individuals with mild cognitive impairment and AD. Animal studies also show improved general behavioral performance and cognition in normal and diabetic mice after treatment with intranasal insulin. It has also been reported that insulin can affect the stability, production, degradation and aggregation of Aβ, leading to reduced neurotoxicity. However, whether intranasal insulin treatment prevents or ameliorates anesthesia-induced tau hyperphosphorylation, which is crucial to neurodegeneration, has not been reported.

Transgenic mouse models that express AD-causing mutations, i.e., mutation in amyloid precursor protein and presenilin, produce only Aβ plaques and not tau pathology. Whereas transgenic mouse models that express tau mutations seen in FTDP-17 produce only tau pathology and not Aβ plaques. The 3xTg-AD mouse model is a dual model of AD and FTDP-17 in which mutations of two different diseases are expressed to produce both Aβ and tau pathologies. To date no tau mutations have been found in AD patients.

BRIEF SUMMARY OF THE INVENTION

The present invention comprises the use of intranasal insulin to attenuate the hyperphosphorylation of tau, which may occur mainly through up-regulation of protein phosphatase 2A (PP2A) and down-regulation of several tau protein kinases. The method of preventing anesthesia induced memory loss in a subject comprises the step of administering intranasal insulin to the subject prior to administering any anesthesia. Preferably, intranasal insulin is administered a plurality of times prior to anesthesia, such as daily of 20-160 IU insulin for a seven consecutive days.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figures 5A, 5B:
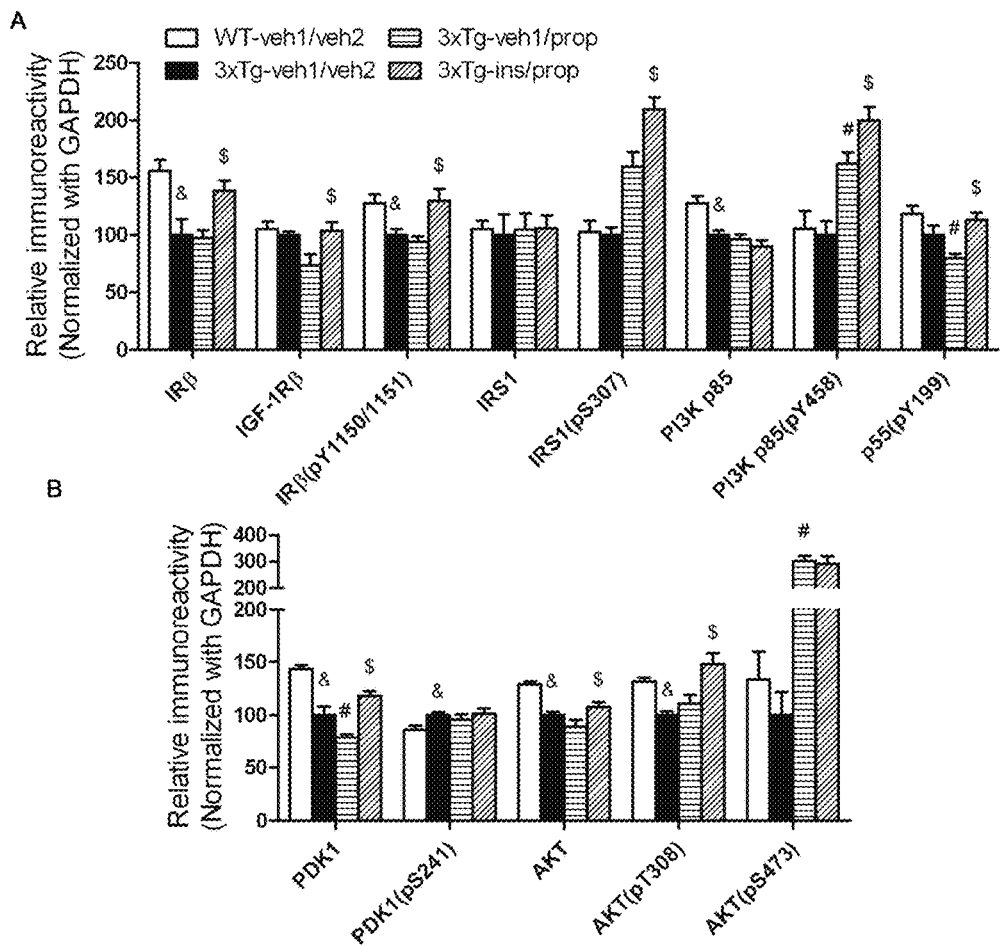

FIGS. 5A and 5B are a series of graphs showing the effect of propofol and intranasal insulin treatment on brain insulin signaling. Homogenates of the rostral halves of brains from mice were sacrificed 30 min following propofol injection and analyzed by Western blots developed with the indicated antibodies. The blots were then quantified densitometrically, and the data are presented as mean±SEM (n=6/group), where the values of the 3xTg-veh1/veh2 group were set as 100%. &p<0.05 vs. WT-veh1/veh2 group; #p<0.05 vs. 3xTg-veh1/veh2 group; $p<0.05 vs. 3xTg-veh1/prop group.

Figure 6A:
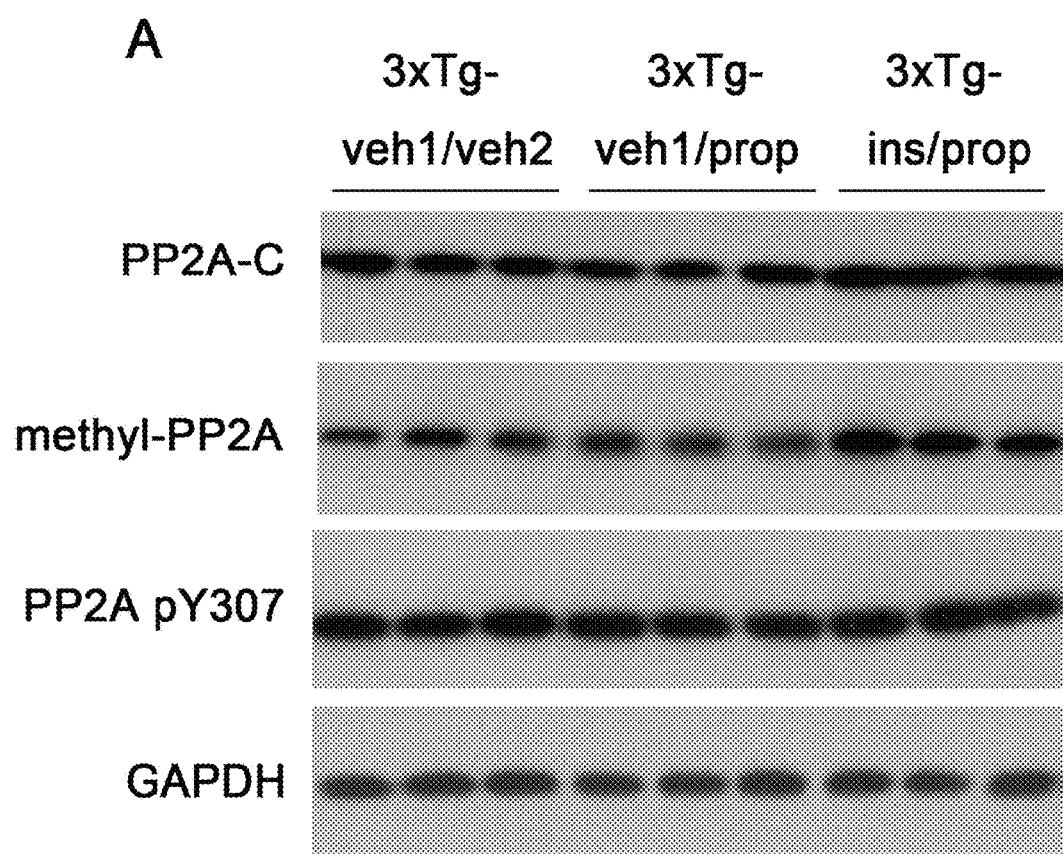
Figure 6B:
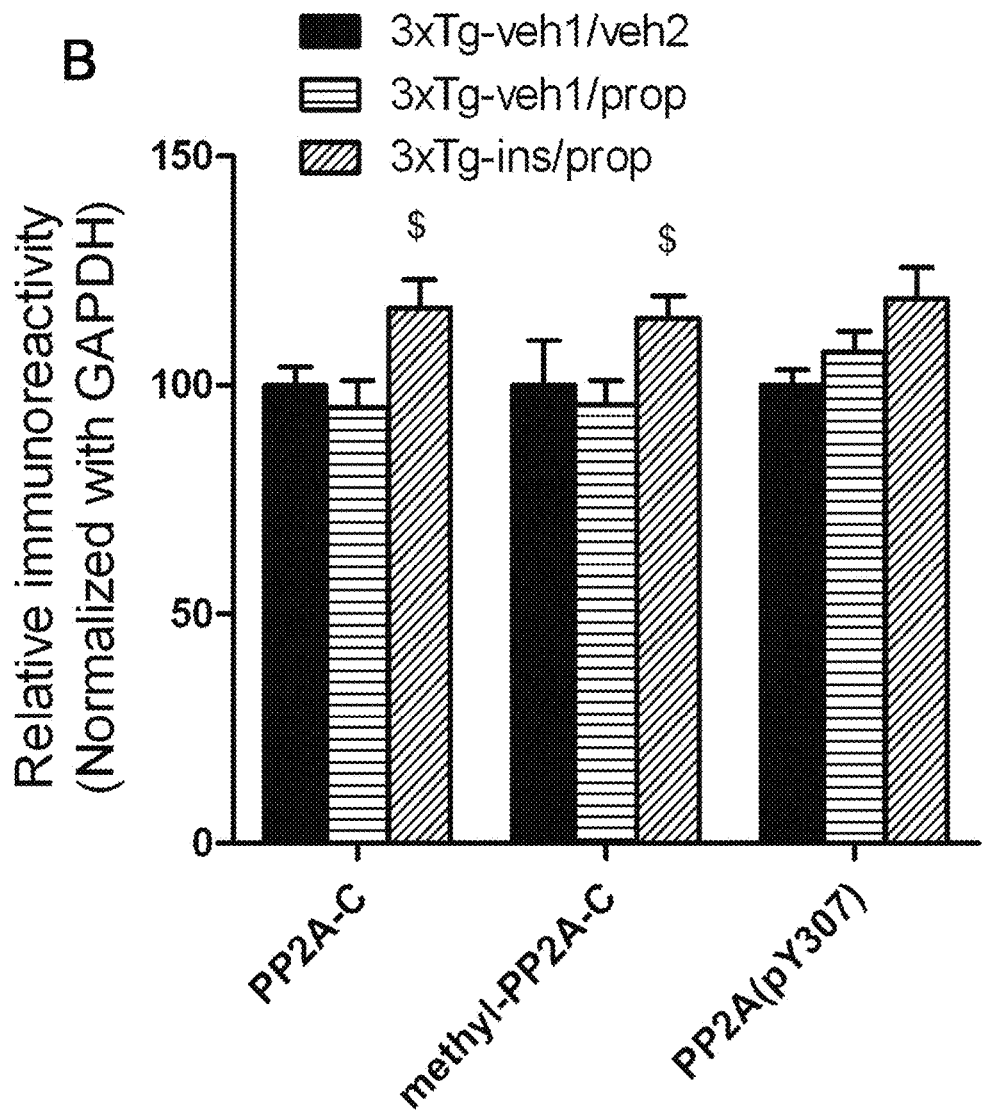
Figure 6C:
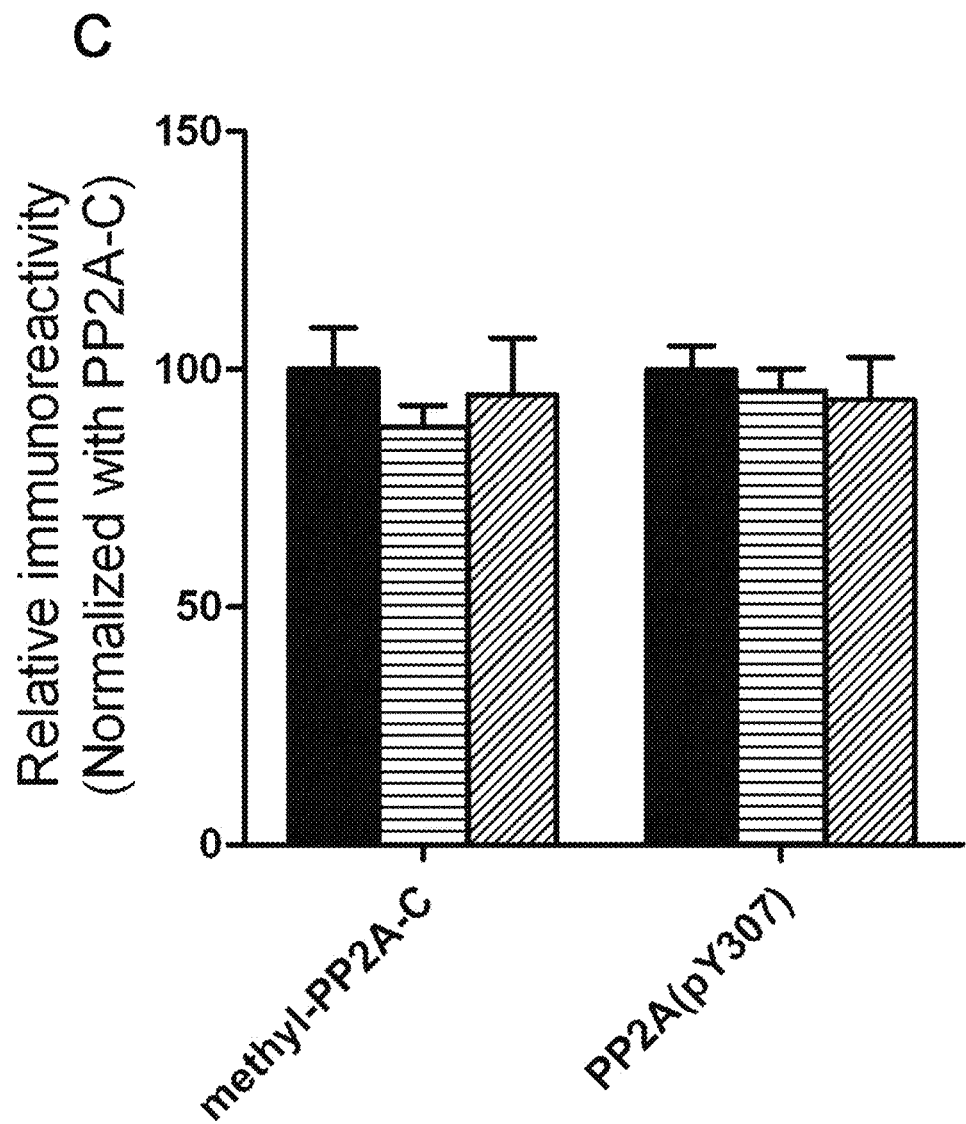

FIG. 6A is a graph of homogenates of the rostral halves of mouse brains analyzed by Western blots developed with antibodies indicated at the left side of the blots;

FIG. 6B is a graph of densitometrical quantifications (mean±SEM, n=6/group) of the blots after normalization with the GAPDH levels, where $ indicates p<0.05 vs. 3xTg-veh1/prop group FIG. 6C is a graph of densitometrical quantifications (mean±SEM, n=6/group) of the blots after normalization with the PP2A-C levels, where $ indicates p<0.05 vs. 3xTg-veh1/prop group.

Figure 7A:
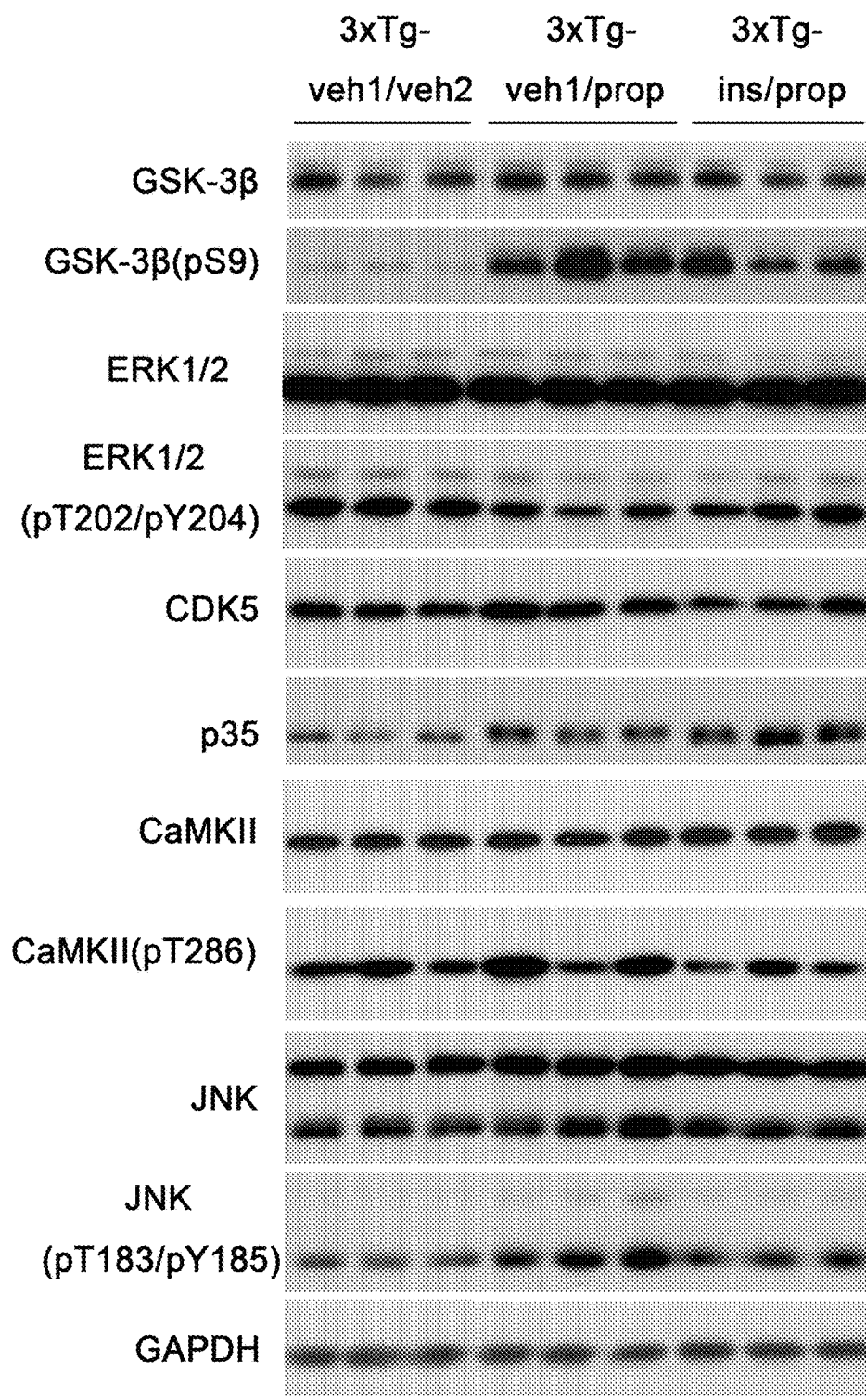
Figure 7B:
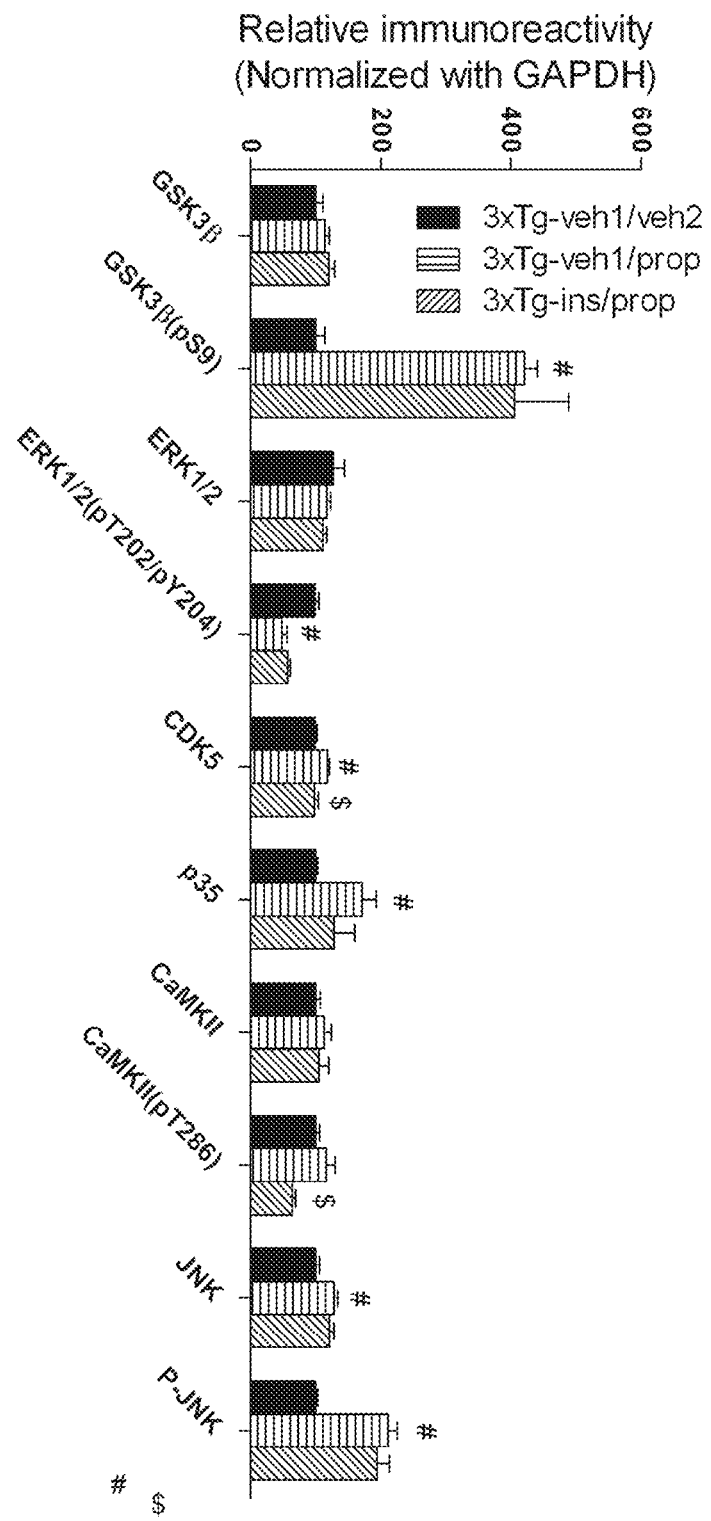
Figure 7C:
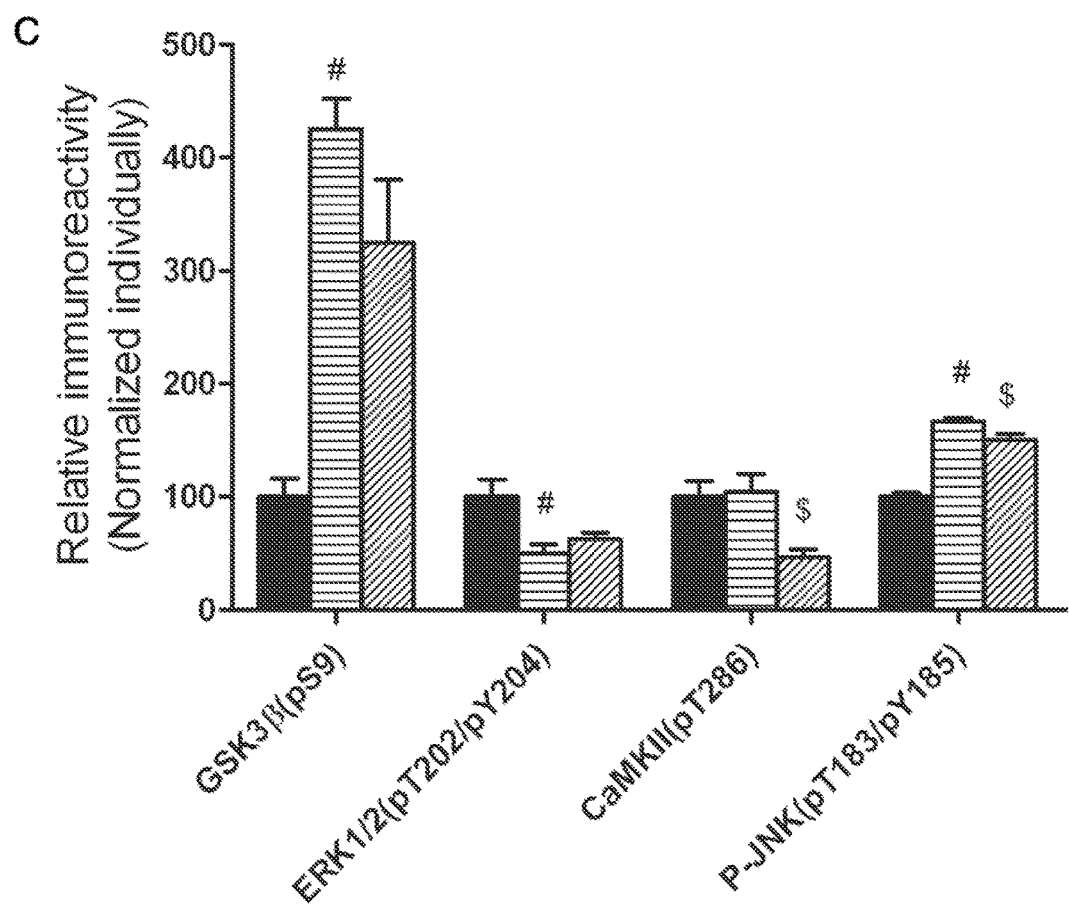
Figure 8A:
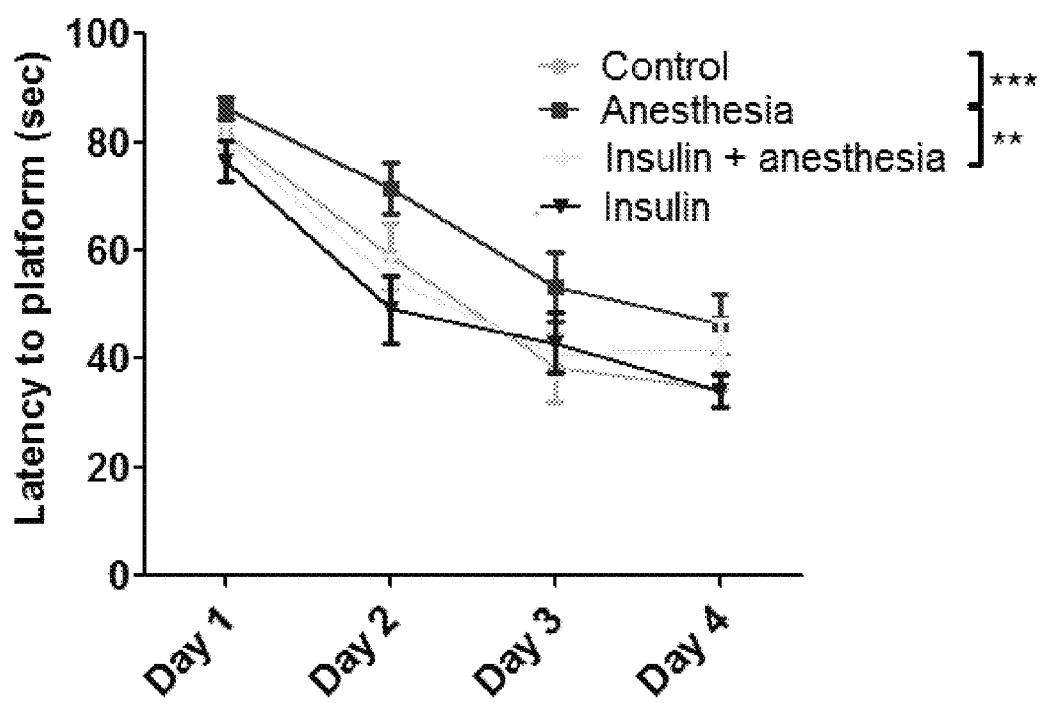
Figure 8B:
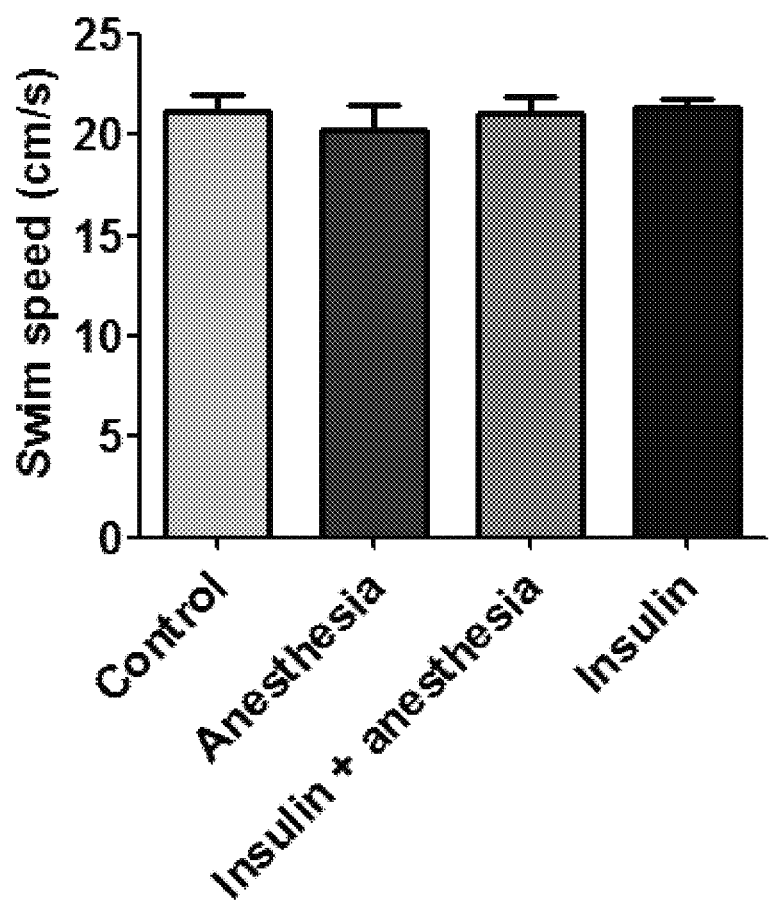
Figure 8C:
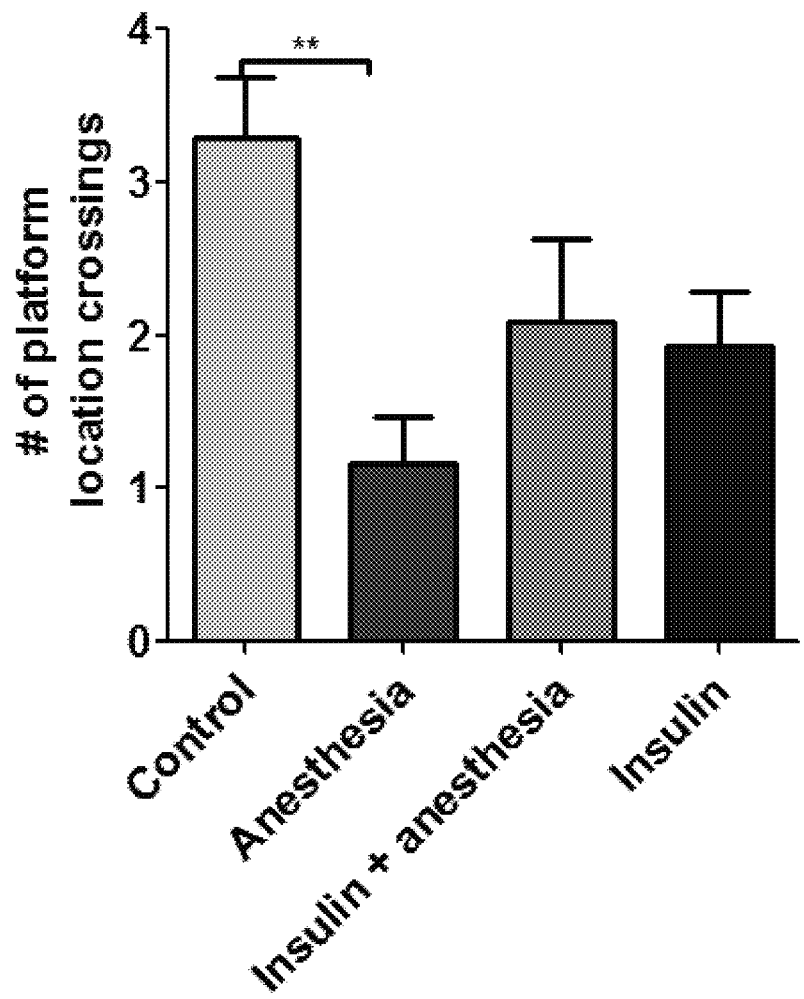
Figure 8D:
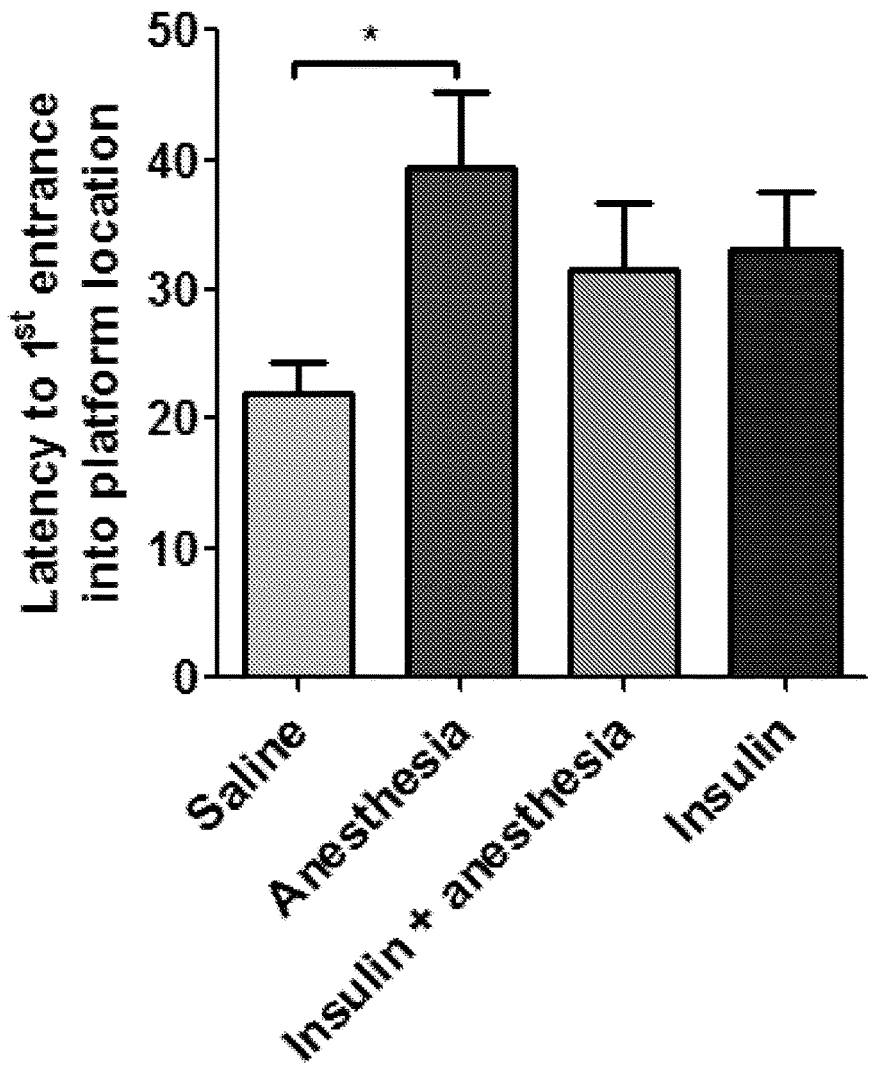

FIG. 7A is a graph showing homogenates of the rostral halves of mouse brains analyzed by Western blots developed with antibodies indicated at the left side of the blots;

FIG. 7B is a graph showing densitometrical quantifications (mean±SEM, n=6/group) of the blots after being normalized with the GAPDH levels, where #p<0.05 vs. 3xTg-veh1/veh2 group; $p<0.05 vs. 3xTg-veh1/prop group;

FIG. 7C is graph showing the levels of the corresponding total protein kinase level, where #p<0.05 vs. 3xTg-veh1/veh2 group; $p<0.05 vs. 3xTg-veh1/prop group;

FIG. 8A is a graph showing latency to reach the hidden platform during the training phase of the Morris water maze task (data shown are the means of four trials tested each day);

FIG. 8B is a graph showing swim speed during the probe test;

FIG. 8C is a graph showing the number of platform location crossings during probe test phase;

FIG. 8D is a graph showing latency to the 1st entrance into the platform location during probe test phase, where all data shown are means±SEM (Control, n=14; Anesthesia, n=12; Insulin+anesthesia, n=12; Insulin, n=14). *, P<0.05; , P<0.01; *, P<0.0001.

DETAILED DESCRIPTION OF THE INVENTION

The present invention involves the finding that anesthesia with propofol exacerbated hyperphosphorylation of tau at multiple abnormally hyperphosphorylated sites in the brain of 3xTg-AD mice and that anesthesia with propofol/sevoflurane caused cognitive impairment in wild type mice. These findings support the role of anesthesia in increasing the risk for tauopathies in vulnerable individuals and demonstrate that anesthesia could be a significant factor for tauopathies in those individuals who have received general anesthesia. The present invention also involves findings that intranasal administration of insulin for a week prior to anesthesia significantly (i) prevented propofol-induced tau hyperphosphorylation and enhanced brain insulin signaling in an accepted mouse model for human tauopathies and (ii) prevented anesthesia-induced cognitive impairment in wild type mice. Thus, intranasal insulin is a promising treatment for prevention of anesthesia-induced memory loss and increased risk for tauopathies. For example, anesthesia induced memory loss or cognitive impairment may be prevented by administering intranasal insulin to a subject prior to administering any anesthesia. Preferably, intranasal insulin is administering once a day for several days prior to the anesthesia, such as consecutively for seven days. The dosage for each administration should be between 20 and 160 IU insulin.

Example 1

In an exemplary study, 3xTg-AD mice, a commonly used transgenic model of AD and tauopathy, which harbors three mutated transgenes (human $PS1_{M146V}$, $APP_{SWE}$, and $tau_{P301L}$), were treated with propofol, a commonly used intravenous anesthetic in clinical practice. The effects of intranasal insulin on propofol-induced hyperphosphorylation of tau were then investigated. Insulin was found to attenuate propofol-induced hyperphosphorylation of tau, which may occur mainly through up-regulation of protein phosphatase 2A (PP2A) and down-regulation of several tau protein kinases.

Materials and Methods

Antibodies and Reagents

Peroxidase-conjugated anti-mouse and anti-rabbit IgG were obtained from Jackson ImmunoResearch Laboratories (West Grove, Pa., USA). The enhanced chemiluminescence (ECL) kit was from Pierce (Rockford, Ill., USA). The ABC staining system was from Santa Cruz Biotechnology (Santa Cruz, Calif., USA). Propofol was purchased from MP Biomedicals (Solon, Ohio, USA). Insulin (Humulin R U-100) was from Eli Lily (Indianapolis, Ind., USA). Other chemicals were from Sigma-Aldrich (St. Louis, Mo., USA).

Animals and Animal Treatments

The breeding pairs of the homozygous 3xTg-AD mouse harboring $PS1_{M146V}$, $APP_{SWE}$ and $tau_{P301L}$ transgenes and the wild type (WT) control mouse (a hybrid of 129/Sv and C57BL/6 mice) were initially obtained from Dr. F. M. LaFerla through Jackson Laboratory (New Harbor, 124 ME, USA), and the mice were bred in our institutional animal colony. Mice were housed (4~5 animals per cage) with a 12/12 h light/dark cycle and with ad libitum access to food and water. The housing, breeding, and animal experiments were in accordance with the approved protocol from an Institutional Animal Care and Use Committee, according to the PHS Policy on Human Care and Use of Laboratory animals (revised Mar. 15, 2010).

Figure 1:
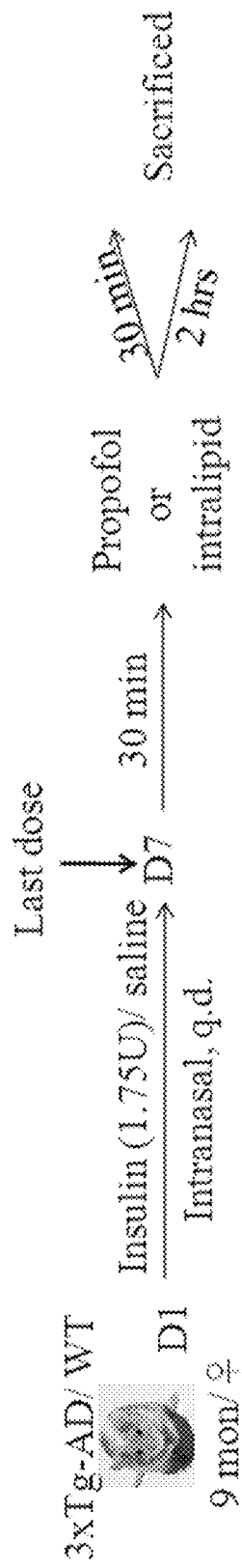
FIG. 1 is a schematic of the animal study design of the present invention.

The 3xTg-AD mice and WT mice (female, 9 months old) used for the present study were habituated to handling for 14 days prior to the experiment. Female mice were used because the female 3xTg-AD mice develop behavioral deficits faster than the male mice. The selection of the age of 9 months was because the 3xTg-AD mice at this age show neurogenic and neuroplastic deficits but no NFTs or amyloid plaques and are cognitively impaired. Intranasal delivery was carried out manually without anesthesia while the mouse head was restrained in a supine position with the neck in extension, as described. A total of 1.75 U/17.5 µl insulin or 0.9% saline (Veh 1) was delivered over both nares alternatively using a 10 µl Eppendorf pipetter. The mouse was held for an additional 5-10 seconds to ensure the fluid was inhaled. The successful nasal delivery by using this approach was confirmed by examination of ink in the autopsied brains after nasal delivery with ink using the same approach (data not shown). All mice were treated with insulin or, as a control, saline daily for 7 consecutive days. Thirty minutes following the last dose, the mice were injected intraperitoneally (i.p.) with propofol dissolved in intralipid (250 mg/kg body weight) or the equivalent amount of intralipid (Veh 2), followed by sacrifice of the animals 30 min or 2 hrs later, as seen in FIG. 1. The brains were removed immediately, and the rostral halves (separated coronally at the bregma level) of the mouse brains were dissected, flash frozen in dry ice, and stored at −80° C. for biochemical analyses at a later date.

Western Blot Analysis

Mouse brain tissue was homogenized in pre-chilled buffer containing 50 mM Tris-HCl (pH 7.4), 50 mM GlcNAc, 20 µM UDP, 2.0 mM EGTA, 2 mM $Na_3VO_4$, 50 mM NaF, 20 mM Glycero-phosphate, 0.5 mM AEBSF, 10 µg/ml aprotinin, 10 μg/ml leupeptin, and 4 μg/ml pepstatin A. Protein concentrations of the homogenates were determined by using modified Lowery method. The samples were resolved in 10% or 12.5% SDS-PAGE and electro-transferred onto Immobilon-P membrane (Millipore, Bedford, Mass., USA). The blots were then probed with primary antibody and developed with the corresponding horseradish peroxidase-conjugated secondary antibody and ECL kit (Pierce, Rockford, Ill.). Densitometrical quantification of protein bands in Western blots were analyzed by using the TINA software (Raytest IsotopenmeBgerate GmbH, Straubenhardt, Germany).

Immunohistochemical Staining

Floating sagittal sections were incubated at room temperature in 0.3% $H_2O_2$ for 30 min and then in 0.3% Triton X-100 for 15 min, washed in PBS, and blocked in a solution containing 5% normal goat serum and 0.1% Triton X-100 for 30 min. Sections were then incubated at 4° C. with primary antibody overnight, followed by incubation with biotinylated secondary antibody and avidin/biotinylated horseradish peroxidase (Santa Cruz Biotechnology). The sections were stained with peroxidase substrate and then mounted on microscope slides (Brain Research Laboratories, Newton, Mass., USA), dehydrated, and covered with coverslips.

Statistical Analysis

For biochemical analyses, data were analyzed by one-way ANOVA followed by Tukey's post hoc tests or unpaired two-tailed t tests, using Graphpad. All data are presented as means±SEM, and $p<0.05$ was considered statistically significant.

Results

Figure 2A:
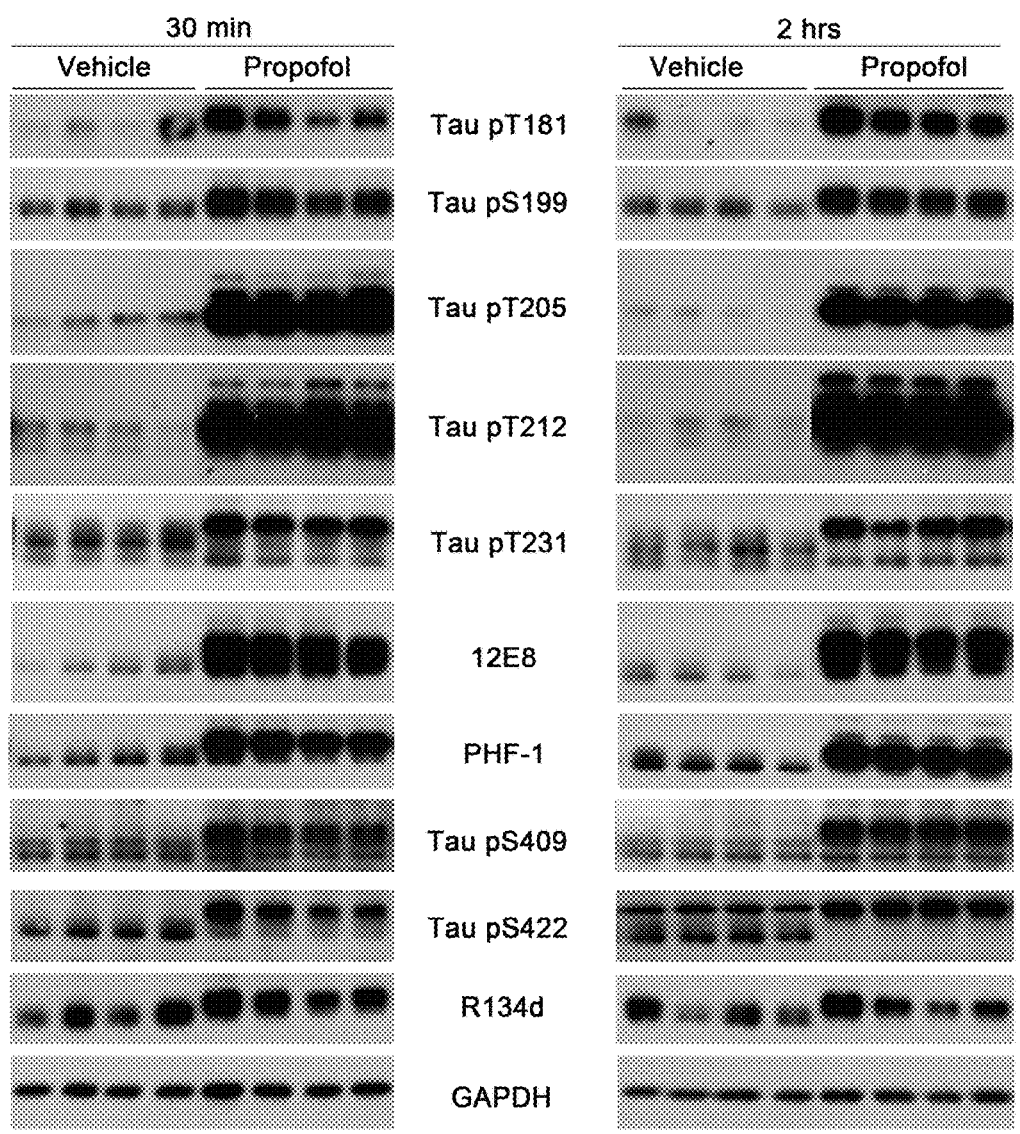
FIG. 2A is series of images of gel electrophoresis showing homogenates of the rostral halves of brains from 3xTg-AD mice sacrificed 30 min or 2 hrs following intraperitoneal injection of propofol were analyzed by Western blots developed with antibody R134d against total tau and several phosphorylation-dependent and site-specific tau antibodies, as indicated in the middle of the blots.
Figures 2B, 2C:
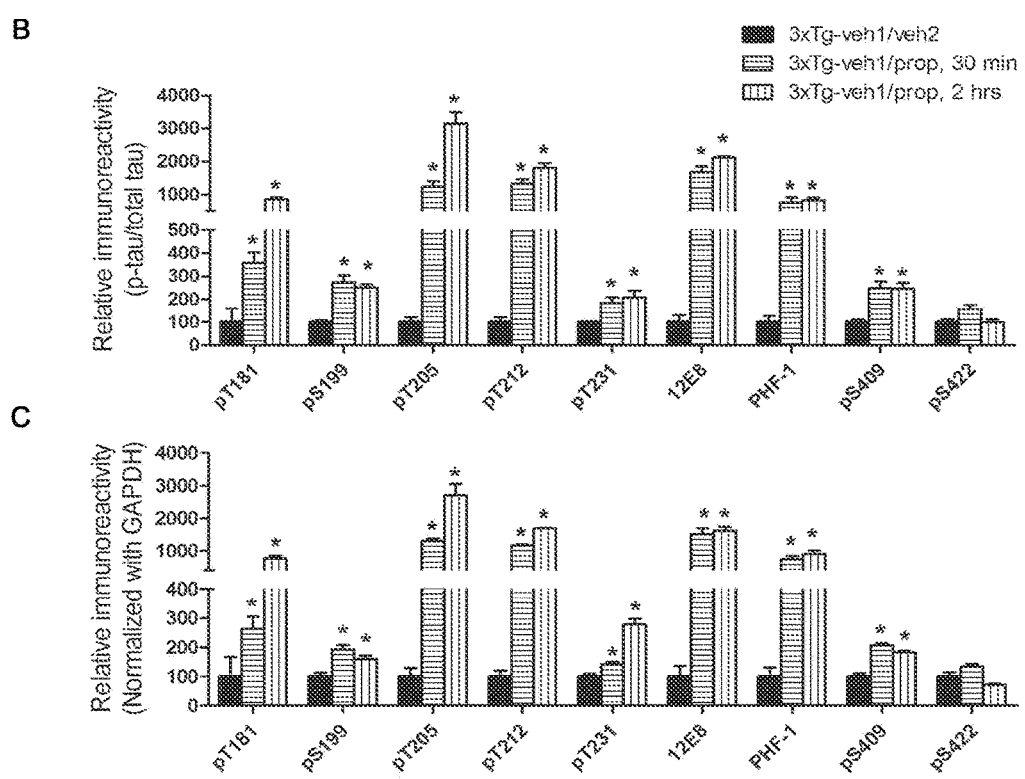
FIGS. 2B and 2C show densitometrical quantifications (mean±SEM, n=6/group) of the blots after being normalized with the corresponding total tau level or with the GAPDH level. The levels of the 3xTg-veh1/veh2 group were set to 100. $*p<0.05$ vs. vehicle-injected 3xTg-AD mice.

Propofol Exacerbates Hyperphosphorylation of Tau at Multiple Sites in 3xTg-AD Mice The effect of propofol treatment on tau phosphorylation was verified by using Western blots developed with phosphorylation-dependent and site-specific tau antibodies, which detect tau phosphorylation at Thr181, Ser199, Thr205, Thr212, Thr231, Ser262/356 (12E8 sites), Ser396/404 (PHF-1 sites), Ser409 and Ser422. As expected, a marked increase in tau phosphorylation was observed at all the above phosphorylation sites except Ser422 both 30 min and 2 hrs after propofol injection, as seen in FIG. 2. Quantitative analyses indicated that the increase of tau phosphorylation was most dramatic at Thr181, Thr205, Thr212, Ser262/356 (12E8 sites), and Ser396/404 (PHF-1 sites), as seen in FIGS. 2B and 2C. The phosphorylation of tau at several sites was higher at 2 hrs than 30 min post anesthesia. Up-shift of the apparent gel mobility of tau, which is a well-established phenomenon of tau hyperphosphorylation, was also seen, as shown in FIG. 2A. These results confirmed marked increase in tau phosphorylation in mice anesthetized with propofol.

Figure 3:
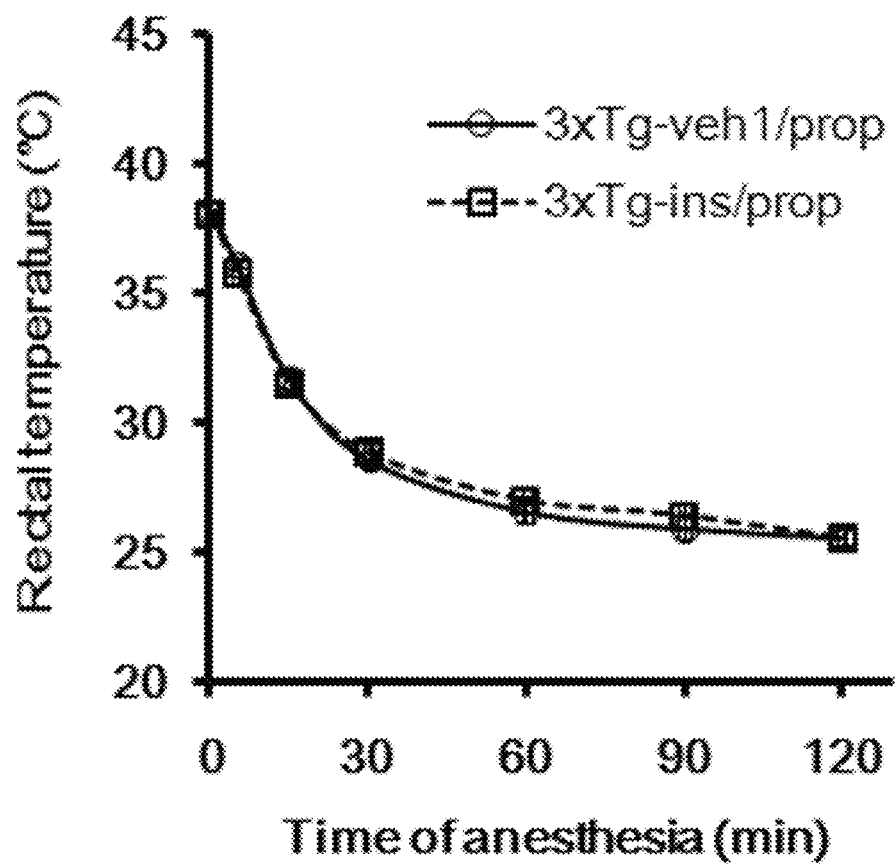
FIG. 3 is a graph of the alteration of rectal temperature during anesthesia of the 3xTg-AD mice.

Hypothermia is known to be a major factor underlying anesthesia-induced tau hyperphosphorylation. Therefore, the rectal temperature of the mice was determined. The average temperature of the mice dropped from around 38.2° C. to 28.6° C. within 30 min after propofol injection, as seen in FIG. 3, which is consistent with previous reports. The average rectal temperature dropped further to 25.6° C. two hours after propofol injection when the mice had not woken from anesthesia.

Intranasal Insulin Attenuates Propofol-Induced Tau Hyperphosphorylation

Figures 4A, 4B:
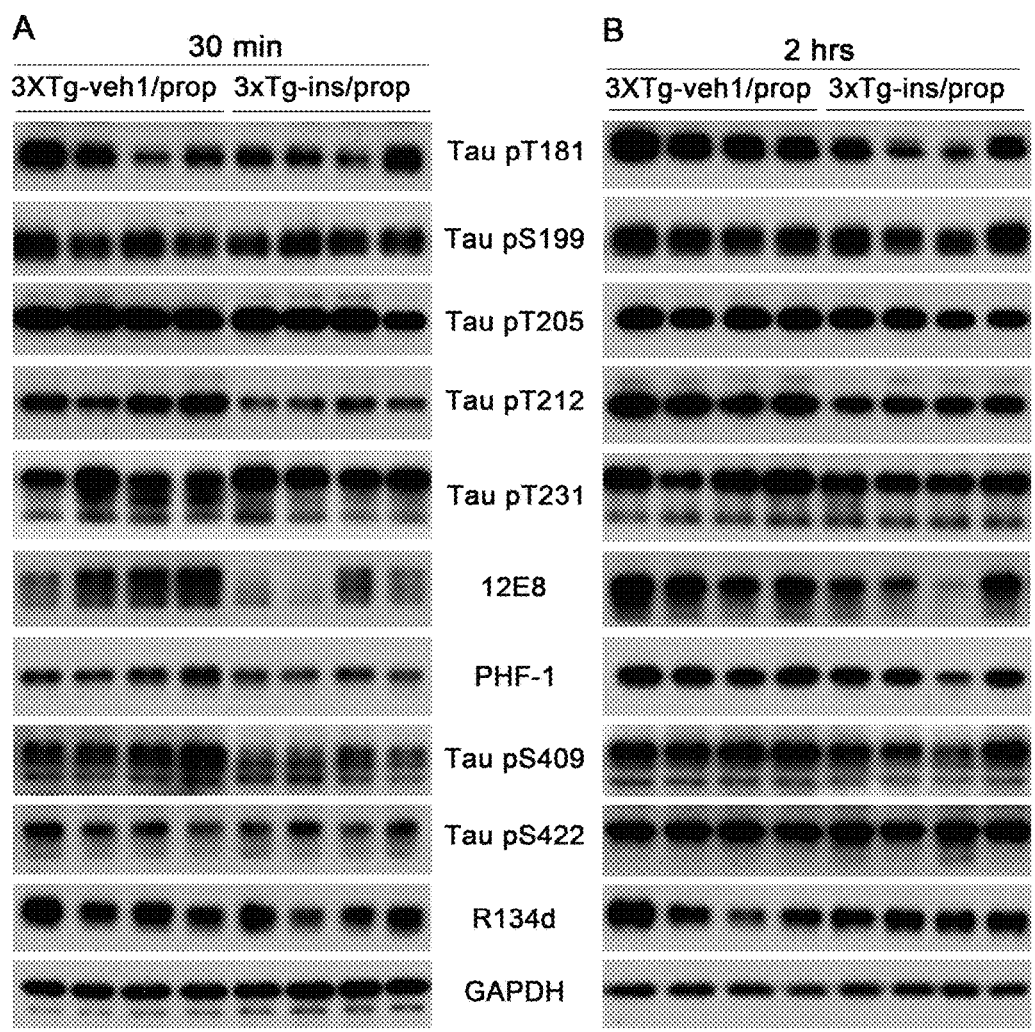
FIGS. 4A and 4B show homogenates of the rostral halves of brains from 3xTg-veh1/prop and 3xTg-ins/prop mice sacrificed 30 min or 2 hrs, respectively, following intraperitoneal injection of propofol and were analyzed by Western blots developed with antibody R134d against total tau and several phosphorylation-dependent and site-specific tau antibodies, as indicated.
Figures 4C, 4D:
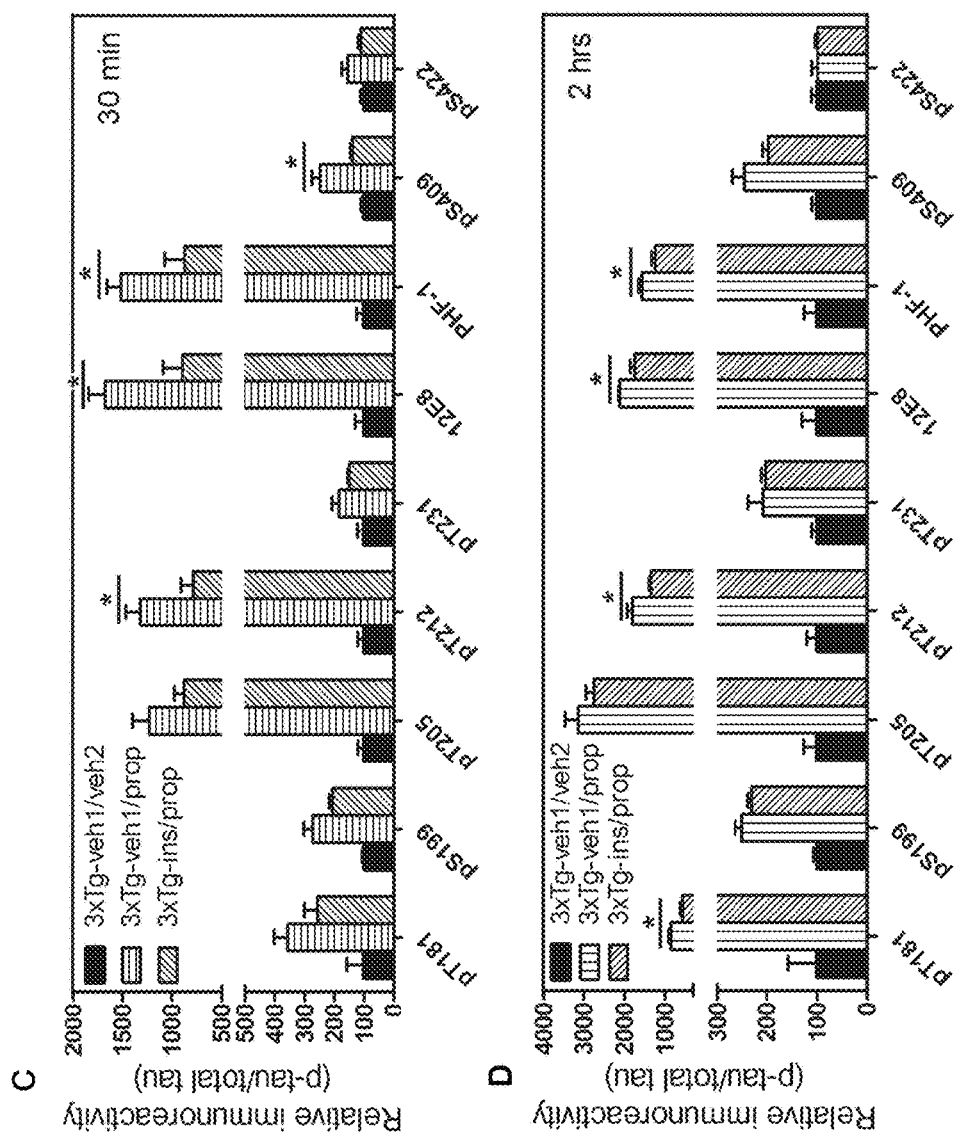
FIGS. 4C and 4D show densitometrical quantifications (mean±SEM, n=6/group) of the blots after being normalized with the corresponding total tau level. $*p<0.05$ m.
Figure 4E:
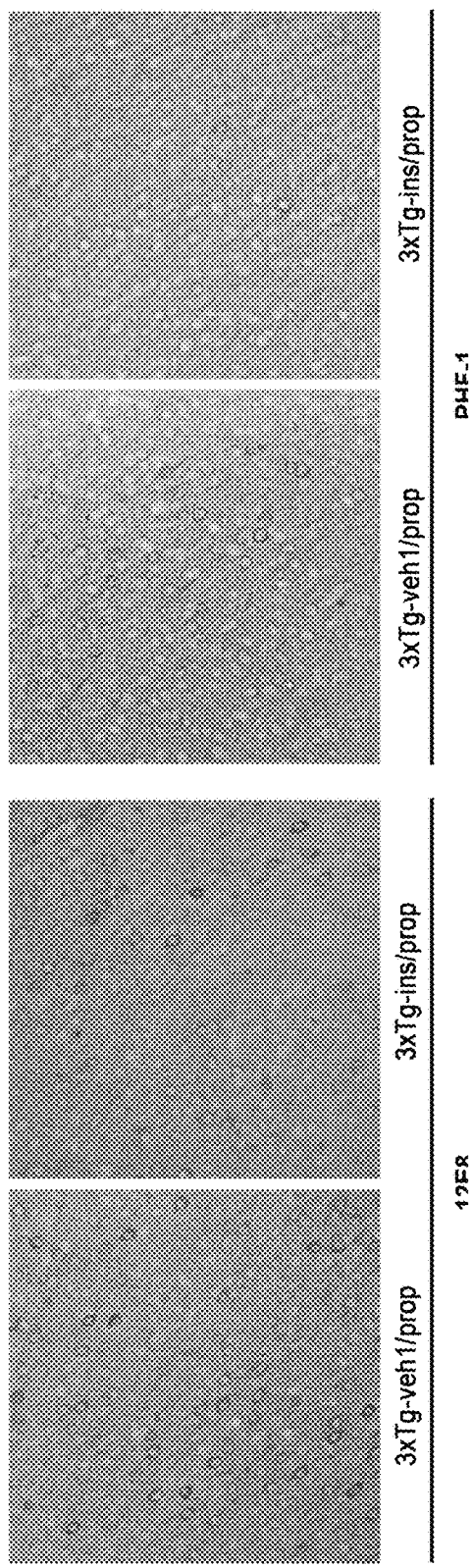
FIG. 4E shows immunohistochemical staining of the brain tissue sections (frontal cortex) of mice sacrificed 30 min after propofol treatment. Monoclonal antibodies 12E8 and PHF-1 recognize tau phosphorylated at Ser262/Ser356 and Ser396/Ser404, respectively.

Insulin is neuroprotective, and intranasal delivery is a non-invasive and effective way for insulin to reach the brain without affecting the peripheral blood glucose level. In order to investigate the effect of insulin on propofol-induced hyperphosphorylation of tau, insulin was delivered intranasally to 3xTg-AD mice for 7 days prior to the administration of propofol. Mice receiving daily intranasal insulin (3xTg-ins/prop group) were observed for seven days before anesthesia had significantly lower phosphorylation level of tau at Thr212, Ser262/356 (12E8 sites), Ser396/404 (PHF-1 sites), and Ser409 at 30 min following propofol injection when compared to mice receiving saline (vehicle) only (3xTg-veh1/prop), as seen in FIGS. 4A and 4C. The phosphorylation level of tau at other epitopes studied (Thr181, Ser199, Thr205, Thr231, and ser422) was also lower in the insulin-treated group than the untreated group, but the decreases did not reach statistical significance, as seen in FIG. 4C. A similar preventive role of insulin against propofol-induced tau phosphorylation was also seen two hours following propofol injection, as seen in FIGS. 4B and 4D. The prevention of tau phosphorylation by insulin was confirmed immunohistochemically by using monoclonal antibodies 12E8 and PHF-1 against phosphorylated tau. The number of strongly stained neurons in the mouse brains was markedly reduced in the 3xTg-ins/prop group as compared to the 3xTg-veh1/prop group, as seen in FIG. 4E. These results indicate that intranasal insulin administration attenuates propofol-induced tau hyperphosphorylation in the mouse brain. The insulin's action in attenuation of propofol-induced tau hyperphosphorylation was not related to hypothermia because no difference in the body temperature between the insulin-treated and untreated mice was observed, as seen in FIG. 3.

Intranasal Insulin Enhances Brain Insulin Signaling

To understand the possible mechanism of the beneficial effect of intranasal insulin treatment on tau hyperphosphorylation, its effect on insulin signaling in the mouse brain was investigating by comparing the level and activation of each component of the signaling pathway, including insulin receptor β (IRβ), insulin-like growth factor-1 receptor β (IGF-1Rβ), insulin receptor substrate-1 (IRS-1), phosphatidylinositide 3-kinases (PI3K), 3-phosphoinositide-dependent protein kinase-1 (PDK1) and protein kinase B (AKT). The activation of these proteins were assessed by measuring their phosphorylation levels at the activity-dependent sites. The insulin signaling pathway was found to be disturbed in the brains of 3xTg-AD mice, as seen in FIGS. 5A and 5B (3xTg-veh1/veh2 vs. WT-veh1/veh2). Propofol further disturbed the insulin signaling, as evidenced by down-regulation of the level of PI3K p55 pY199 and PDK1 and up-regulation of the level of PI3K p85 pY458 and AKT pS473, as seen in FIGS. 5A and 5B. The dramatic increase in AKT pS473 might result from a cross-talk with other signaling pathway activated by propofol. The intranasal delivery of insulin for 7 days prior to the administration of propofol enhanced the insulin signaling transduction in the brain. The levels of IRβ, IGF-1Rβ, IRβ pY1150/1151, IRS1 pS307, PI3K p85 pY458, PI3K p55 pY199, PDK1, AKT and AKT pT308 were all up-regulated in the 3xTg-ins/prop mice as compared to the 3xTg-veh1/prop mice, as see in FIG. 5. These results indicate that intranasal insulin promotes brain insulin signaling.

Intranasal Insulin Up-Regulates PP2A in the Brain

Down-regulation of PP2A, a major tau phosphatase in the brain, was shown to underlie anesthesia-induced hyperphosphorylation of tau. To investigate whether PP2A also mediates insulin's activity to attenuate propofol-induced tau hyperphosphorylation, the level of the catalytic subunit of PP2A (PP2A-C) and its methylation, which enhances PP2A activity,[39] and tyrosine-phosphorylation at Tyr307, which inhibits its activity, was determined. Intranasal insulin treatment led to a significant increase in the level and the methylation of PP2A in the mouse brain, as seen in FIGS. 6A and 6B. However, the net PP2A methylation, as quantified after normalization with the PP2A-C level, was not increased as seen in FIG. 6C, suggesting that the increased total PP2A methylation is due to the increase of PP2A-C level. These results suggest that intranasal insulin might attenuate propofol-induced tau hyperphosphorylation through an increase of methylated PP2A-C and thus its activity in the brain.

Activities of Several Tau Kinases are Altered in the Mouse Brain after Propofol and Intranasal Insulin Treatments Besides PP2A, tau phosphorylation is also regulated by several protein kinases. The levels of several tau protein kinases have been reported to be altered after anesthesia. We therefore determined the levels of the total and the activated form of several tau protein kinases, including glycogen synthase kinase-3β (GSK-3β), mitogen-activated protein kinase/extracellular signal-regulated kinase (MAPK/ERK), cyclin-dependent kinase 5 (cdk5), calcium/calmodulin-dependent protein kinase II (CaMKII), and c-Jun N-terminal kinase (JNK). Consistent with previous studies, a dramatic increase in the inhibitory Ser9 phosphorylation of GSK-3β and moderate alterations of a few other tau kinases after anesthesia with propofol was found, as seen in FIG. 7. Intranasal insulin treatment resulted in mild to moderate reductions of CDK5, CaMKII pT286 and JNK pT184/pY185 in the propofol-treated mouse brains. These results suggest that the insulin-induced reduction of these three tau kinases might also contribute to insulin's role in attenuation of propofol-induced tau hyperphosphorylation.

Discussion

Tau is the major microtubule-associated protein of mature neurons. Its major known physiological activity is to promote the assembly of tubulin into microtubules and to stabilize microtubule structure. Abnormally hyperphosphorylated tau fails to bind to tubulin and also gains a toxic activity of disrupting microtubules. Therefore, abnormal hyperphosphorylation of tau appears to be crucial to neurodegeneration in tauopathies including AD. The vital role of tau in neurodegeneration have been further supported by several recent in vivo studies showing that tau knockout reduces or eliminates neurodegeneration and behavioral deficits in transgenic mouse models of AD.

Many epidemiological studies have demonstrated that general anesthesia induces memory loss and increases the risk for dementia and AD. In an effort to understand the possible underlying mechanisms, several studies have found that both intravenous and inhalational anesthetics induce hyperphosphorylation of tau in the brain. These studies suggest an important molecular mechanism by which anesthesia may induces memory loss and increases the risk for dementia and AD through promoting abnormal hyperphosphorylation of tau and consequently neurodegeneration.

It has been reported that anesthetics induced hyperphosphorylation of tau is a consequence of PP2A inhibition by hypothermia. Subsequently, two distinct underlying mechanisms were found: one associating with activation of stress-activated protein kinases and the other resulting from anesthesia-induced hypothermia. Consistent with previous reports, the present study showed a marked increase in tau phosphorylation at several AD-related sites after 3xTg-AD mice were anesthetized with propofol. Furthermore, tau hyperphosphorylation was accompanied with activation of JNK but inhibition of GSK-3β and ERK after anesthesia with propofol. These findings are consistent with previous observations showing activation of JNK and marked inhibition of GSK-3β and ERK in wild type mice after anesthesia.

Drug administration into the brain through intranasal delivery bypasses the blood brain barrier and has been used successfully in animal studies and clinical trials in humans. Intranasal administration of insulin has an additional advantage that it does not interfere with the insulin level or glucose metabolism in the periphery. Thus, the present invention applied this approach to investigate whether insulin prevents or ameliorates anesthesia-induced tau hyperphosphorylation. Daily administration of insulin for a week significantly prevented propofol-induced tau hyperphosphorylation at several AD-related sites. Furthermore, the preventive role of insulin might result from its promotion of brain insulin signaling and PP2A and down-regulation of several tau protein kinases, CDK5, CaMKII and JNK. Although hypothermia was observed in the 3xTg-AD mice after anesthesia with propofol, the preventive role does not seem to be associated with hypothermia because pre-treatment of mice with intranasal insulin did not affect propofol-induced hypothermia. These findings provide important evidence supporting the use of intranasal insulin treatment for preventing anesthesia-induced risk for memory loss and dementia.

Example 2

In another experiment to investigate whether intranasal administration can prevent anesthesia-induced cognitive impairment, we treated old (age of 17-18 months) wild type mice with daily intranasal administration of insulin (1.75 IU/mouse/day) for seven consecutive days before anesthesia induced with intraperitoneal injection of propofol (150 mg/kg) followed by sevoflurane (2.5%) inhalation for one hour. This paradigm of anesthesia is similar to that used clinically for surgical patents in the U.S. The cognitive function of the mice was assessed starting on the next day by using the Morris water maze (MWM) test, a widely used cognitive test for rodents.

Learning curves of mice in the MWM is a standard way to demonstrate their spatial learning ability. As shown in FIG. 8A, the control mice (no insulin or anesthesia) showed normal learning, as evidenced by continuous decrease in the time needed to reach the escape platform during the four training days in water maze. Mice after one-time anesthesia demonstrated impaired learning in the following four days because they took a longer time to reach the platform. The learning performance of the insulin-treated mice before one-time anesthesia was found to be as good as control mice, indicating that the daily intranasal administration of insulin for seven days can prevent anesthesia-induced impairment in spatial learning. The insulin treatment to control mice without anesthesia did not affect spatial learning significantly. The swimming speeds of the mice among the four groups were not different, as seen in FIG. 8B, which otherwise would affect the learning curves.

Probe testing was carried out on the following day after four-day training and was used to evaluate the retrieval of spatial memory. As compared to the control mice, the anesthetic mice crossed the platform location much less times, as seen in FIG. 8C, and took a longer time to reach the platform location, as seen in FIG. 8D, during a 60-second test period, indicating a marked deficit in the retrieval of spatial memory 5 days after anesthesia. Mice with insulin treatment before anesthesia showed increased number of platform location crossing, as seen in FIG. 8C, orange vs.

red, and decreased time to reach the platform location, as seen FIG. 1D, suggesting that the daily intranasal administration of insulin for seven days may also prevent anesthesia-induced impairment in spatial memory.

What is claimed is:

1. A method of minimizing anesthesia induced memory loss in a subject in need thereof, comprising the step of administering intranasal insulin to the subject prior to administering any anesthesia.

2. The method of claim 1, wherein the step of administering intranasal insulin comprises administering intranasal insulin a plurality of times.

3. The method of claim 2, wherein administering intranasal insulin a plurality of times comprises administering intranasal insulin daily for a predetermined number of days prior to administering anesthesia.

4. The method of claim 3, wherein the predetermined number of days is seven.

5. The method of claim 4, wherein the seven days are consecutive.

6. The method of claim 1, wherein the step of administering intranasal insulin to the subject prior to administering any anesthesia comprises administering a dose of between 20 and 160 IU insulin.

* * * * *